(12) United States Patent
Su et al.

(10) Patent No.: US 10,806,762 B2
(45) Date of Patent: Oct. 20, 2020

(54) METHOD OF TREATMENT OF CANCER CELLS BY USING PHARMACEUTICAL COMPOSITION

(71) Applicants: TAIWAN INDIGENA BOTANICA CO., LTD., Taipei (TW); TAIPEI MEDICAL UNIVERSITY, Taipei (TW)

(72) Inventors: Ching-Hua Su, Taipei (TW); Cheng-Jeng Tai, Taipei (TW); Yeu-Ching Shi, New Taipei (TW)

(73) Assignees: TAIWAN INDIGENA BOTANICA CO., LTD., Taipei (TW); TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 16/275,317

(22) Filed: Feb. 13, 2019

(65) Prior Publication Data
US 2019/0175674 A1   Jun. 13, 2019

Related U.S. Application Data

(62) Division of application No. 15/384,384, filed on Dec. 20, 2016, now abandoned.

(30) Foreign Application Priority Data

May 20, 2016 (TW) .............................. 105115737 A

(51) Int. Cl.
A61K 36/074 (2006.01)
A61K 36/07 (2006.01)

(52) U.S. Cl.
CPC ............ *A61K 36/074* (2013.01); *A61K 36/07* (2013.01); *A61K 2236/33* (2013.01); *A61K 2236/331* (2013.01)

(58) Field of Classification Search
None
See application file for complete search history.

(56) References Cited

U.S. PATENT DOCUMENTS

| 7,135,183 | B1 | 11/2006 | Wang et al. | |
| 10,131,716 | B2* | 11/2018 | Tai | A61K 31/726 |
| 10,195,238 | B2* | 2/2019 | Tai | A61K 36/07 |
| 2003/0148517 | A1 | 8/2003 | Chen et al. | |
| 2009/0280062 | A1 | 11/2009 | Wong et al. | |
| 2010/0210869 | A1 | 8/2010 | Wu et al. | |
| 2014/0134153 | A1 | 5/2014 | Iwahara et al. | |
| 2014/0328872 | A1* | 11/2014 | Wang | A61K 36/484 424/195.15 |
| 2017/0224752 | A1 | 8/2017 | Tai et al. | |
| 2017/0333502 | A1* | 11/2017 | Su | A61K 36/07 |
| 2019/0151386 | A1* | 5/2019 | Huang | A61K 36/074 |

FOREIGN PATENT DOCUMENTS

CN    101559084 A  * 10/2009

OTHER PUBLICATIONS

Lin, L. et al. The Ethanolic Extract of Taiwanofungus camphoratus Induces Cell Cycle Arrest . . . BioMed Research Int pp. 1-10. (Year: 2015).*
Popovic V. et al. Mycotherapy of Cancer: An Update on Cytotoxic and Antitumor Activities of Mushrooms . . . Current Topics in Medicinal Chemistry 13(21)2791-2806, 2013. (Year: 2013).*
Ng T. et al. Low MW Compounds with Anticancer Activity of Mushroom Origin. Int J of Cancer Research and Prevention 7(3-4)301-312 Dec. 2014. (Year: 2014).*
Vetchinkina E. et al. Antitumor Activity of Extracts from Medicinal Basidiomycetes Mushrooms. Int J of Medicinal Mushrooms 18(11) 955-964 2016. (Year: 2016).
Lee. S. et al. Antitumor Effects of Polysaccharides of Ganoderma Lucidum. Int of Medicinal Mushrooms 6(1)1-16 2003. (Year: 2013).
Chen P. et al. Isolation and Synthesis of Bioactive Benzenoid Derivative from the Fruiting Bodies of Antrodia camphorata. Molecules 18(7)7600-7608 2013. (Year: 2013).
Chen L. et al. Preparation of Micellar Oarl Dosage Form of Amphotericin B for Synergistic Enhancement of Anticancer Effects with the Pretreatment of Ethanolic Extract of Taiwanofungus camphoratus. European J of Cancer 50(Suppl 5) 814, 2014. (Year : 2014).
Thyagarajan A. et al. Triterpenes from Ganoderma lucidum Induce Autophagy in Colon Caner Through the Inhibition of p38. Nutrition and Cancer 65(5)630-640 Jul. 2010. (Year: 2010).
Chen L. et al. Pretreatment with an Ethanolic Extract of Taiwanofungus camphoratus Enhances the Cytotoxic Effects of Amphotericin B. J of Agricultural and Food Chemistry 59(20) 11255-11263, 2011. (Year: 2011).

* cited by examiner

*Primary Examiner* — Ralph J Gitomer
(74) *Attorney, Agent, or Firm* — Anova Law Group, PLLC

(57) ABSTRACT

Disclosures of the present invention describe a method of treatment of cancer cells by using pharmaceutical composition. In the present invention, it particularly adopts an ethanol extract of *Taiwanofungus camphorata* (TCEE), an ethanol extract of *Ganoderma lucidum* (GLEE) or a combination of the TCEE and the GLEE as the a pharmaceutical composition for use in causing the apoptosis of lung cancer cells A594, hepatoma cells Huh 7, breast cancer cells MDA-MB 231, and colorectal cancer cells HT 29. Moreover, related experimental data have proved that, the pharmaceutical composition can not only be used for adjunctively treating cancer, but also possesses many healthy effects, including: detoxification, enhancing immunity, and increasing appetite.

2 Claims, 4 Drawing Sheets

METHOD OF TREATMENT OF CANCER CELLS BY USING PHARMACEUTICAL COMPOSITION

CROSS-REFERENCE TO RELATED APPLICATIONS

This application is a divisional application of U.S. patent application Ser. No. 15/384,384 filed on Dec. 20, 2016 entitled "PHARMACEUTICAL COMPOSITION FOR ADJUNCTIVELY TREATING CANCER".

BACKGROUND OF THE INVENTION

1. Field of the Invention

The present invention relates to the technology field of medically-used compositions, and more particularly to a method of treatment of cancer cells by using pharmaceutical composition.

2. Description of the Prior Art

Census report made by Health and Welfare Ministry of Taiwan indicates that, the number of Taiwanese suffered with cancer in 2013 has increased 2499 compared to last year. Moreover, it is worth noting that, summation of the numbers of Taiwanese suffered with colorectal cancer, lung cancer, liver cancer, and breast cancer is about 50 percent of the total cancer patients.

Currently, the primary therapeutic treatment for lung cancer is surgical removal. However, most people are not diagnosed with lung cancer until late in the disease process. So that, after removing the major lesions of lung cancer, the doctors commonly apply a radiation treatment to those locally advanced cancer. However, as healthcare personnel well knows that radiation therapy for lung cancer would cause some side-effects to the lung cancer patients, such as fatigue, lethargy, poor appetite, skin peeling, and radiation pneumonitis. Therefore, how to provide a therapeutic treatment or drug to substitute for the radiation treatment has become an important issue.

In clinical, therapeutic treatments for liver cancer are divided into surgical treatments and non-surgical treatments, wherein the surgical treatments includes: hepatic artery embolization, ethanol injection, radiofrequency electric heat treatment, and chemical treatment. Hepatic artery embolization is a general therapeutic treatment for curing small liver cancer, and can effectively cause the apoptosis of liver cancer cells with the use of anticancer drugs or radiation substances. However, a great number of clinical cases have proved that, the radiation substances would not only cause liver fibrosis become more badly but also induce other side-effects. Therefore, how to develop a therapeutic treatment or drug to substitute for the radiation substances has become an important study target.

Similarly, therapeutic ways for breast cancer includes: surgical removal, radiation therapy, chemotherapy and hormone therapy. After removing the major lesions of breast cancer, the doctors often adopt chemotherapy as an adjunctive treatment for reducing the recurrence of breast cancer. Chemotherapy is a type of cancer treatment that uses anticancer drugs to destroy cancer cells. However, a great number of clinical cases have proved that, the chemotherapy may induce some side-effects, for example, nausea, vomiting, poor appetite, diarrhea, hair loss, mouth ulcers, and decreased hematopoietic function. Therefore, how to develop a therapeutic treatment or drug to substitute for the chemotherapy has become an important issue.

Because colorectal cancer cells often transfer to liver, lung and bone through lymph or blood, some microscopic metastasis of colorectal cancer may exist in patient body even if the major lesions of colorectal cancer have been surgically removed. For this reason, the doctors often adopt adjunctive chemotherapy to reduce the colorectal cancer's recurrence after the surgical removal. However, some acute side-effects may be commonly induced after treating the chemotherapy to the patient, such as diarrhea and inflammation of perineum skin. Moreover, the chemotherapy for colorectal cancer may also cause other chronic side-effects to the patient, for example, obstruction, bleeding, perforation, and necrosis of small intestine.

From above descriptions, it can easily know that combination treatment of surgical removal and chemotherapy (or radiation therapy) is commonly adopted by doctors for curing the lung cancer, liver cancer, breast cancer, and colorectal cancer. So that, in view of all of chemotherapies and radiation therapies would cause side-effects to cancer patients, the inventor of the present application has made great efforts to make inventive research thereon and eventually provided a method of treatment of cancer cells by using pharmaceutical composition.

SUMMARY OF THE INVENTION

The primary objective of the present invention is to provide a method of treatment of cancer cells by using pharmaceutical composition. In the present invention, it particularly adopts an ethanol extract of *Taiwanofungus camphorata* (TCEE), an ethanol extract of *Ganoderma lucidum* (GLEE) or a combination of the TCEE and the GLEE as the a pharmaceutical composition for use in causing the apoptosis of lung cancer cells A594, hepatoma cells Huh 7, breast cancer cells MDA-MB 231, and colorectal cancer cells HT 29. Moreover, related experimental data have proved that, the pharmaceutical composition can not only be used for adjunctively treating cancer, but also possesses many healthy effects, including: detoxification, enhancing immunity, and increasing appetite.

In order to achieve the primary objective of the present invention, the inventor of the present invention provides a first embodiment of the method of treatment of cancer cells by using pharmaceutical composition, wherein the pharmaceutical composition is provided by mixing an ethanol extract of *Taiwanofungus camphorata* (TCEE) and an ethanol extract of *Ganoderma lucidum* (GLEE) based on a mixing ratio in a range from 1:11 to 10:1, and the method comprising treating cancer cells selected from the group consisting of lung cancer cell A549, liver cancer cell Huh 7, breast cancer cell MDA-MB 231, and colorectal cancer cell HT 29 with the pharmaceutical composition by an dosage in a range from 50 µg/mL to 250 µg/mL, thereby exhibiting a therapeutic effect to a cancer tumor constituted by the cancer cells.

In the embodiment of the method, the specific cancer is selected from the group consisting of: lung cancer, liver cancer, breast cancer, and colorectal cancer.

In the embodiment of the method, the pharmaceutical composition reduces the cell viability of the cancer cells down to 50%.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
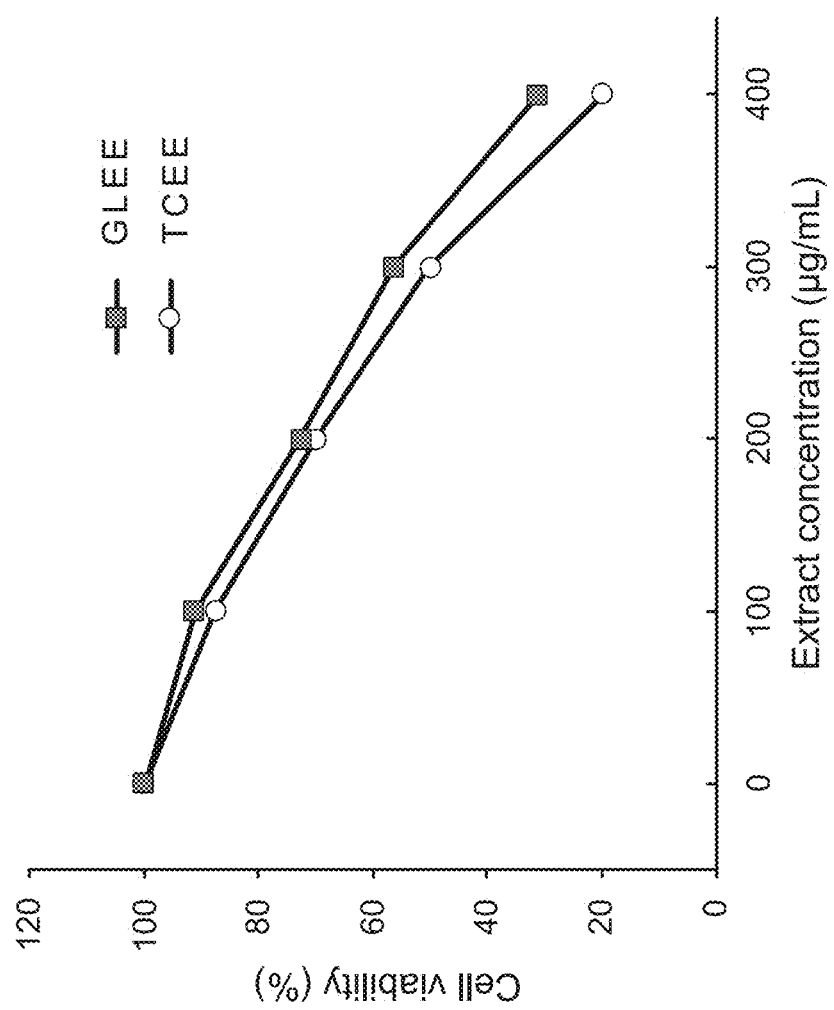
FIG. 1 shows a plot curve graph of extract concentration versus cell viability.

To more clearly describe a method of treatment of cancer cells by using pharmaceutical composition according to the present invention, embodiments of the present invention will be described in detail with reference to the attached drawings hereinafter.

*Antrodia camphorata* is one kind of expensive medicinal fungus. Because the source place of the *Antrodia camphorata* is in Taiwan, the *Antrodia camphorata* is also called *Taiwanofungus camphorata*. The artificial cultivation ways for the *Taiwanofungus camphorata* can be divided into liquid fermentation, solid cultivation and the basswood cultivation. Moreover, researching and studying data have proved that the basswood cultivated *Taiwanofungus camphorata* possesses excellent antioxidant and anticancer ingredients.

The first embodiment of the pharmaceutical composition for adjunctively treating cancer is a *Taiwanofungus camphorata* extract, wherein the *Taiwanofungus camphorata* extract is a water extract of *Taiwanofungus camphorata* (TCWE) or an ethanol extract of *Taiwanofungus camphorata* (TCEE).

In the present invention, the TCEE is taken as an exemplary embodiment for proving the therapeutic effect of the pharmaceutical composition to a specific cancer. The TCEE is fabricated by using following processing steps:

step (1): preparing 10-gram dried fruiting body of a *Taiwanofungus camphorata*, and using ethanol of 400 mL to treating the dried fruiting bodies with a first extracting process under 45-60° C., for 24 hours;

step (2): filtering a first extract liquid collected from the step (1), and then obtaining a first filtrate liquid and a post-extraction residue of the *Taiwanofungus camphorata*;

step (3): using ethanol of 400 mL to treating the post-extraction residue with a second extracting process under 45-60° C., for 24 hours;

step (4): filtering a second extract liquid collected from the step (3), and then obtaining a second filtrate liquid;

step (5): mixing the first filtrate liquid and the second filtrate liquid for obtaining a mixture liquid, and then using a Termovap Nitrogen Sample Concentrator to make the mixture liquid become thick and dense;

step (6): adding dimethyl sulfoxide (DMSO) of 1-2 mL into the mixture liquid, so as to obtain a sample liquid;

step (7): filtering the sample liquid by using a filtration film having pore size of 0.22-0.45 µm, and then taking the sample liquid with a suitable dose (0-250 µg/mL) for cell experiments.

As the person skilled in fungus technology field well knows, Lingzhi mushroom (or Reishi mushroom) is considered to be Ganodermataceae in a board sense. However, in the narrow sense, Lingzhi mushroom means some special species be widely cultivated. Lingzhi mushroom is found having a variety of healthcare effects, and can be divided into red mushroom (*Ganoderma lucidum*), yellow mushroom, white mushroom, green mushroom, black mushroom, and purple mushroom. The second embodiment of the pharmaceutical composition for adjunctively treating cancer is a *Ganoderma lucidum* extract, wherein the *Ganoderma lucidum* extract is a water extract of *Ganoderma lucidum* (GLWE) or an ethanol extract of *Ganoderma lucidum* (GLEE). Moreover, in the present invention, the GLEE is taken as an exemplary embodiment for proving the therapeutic effect of the pharmaceutical composition to a specific cancer. The GLEE is fabricated by using above-mentioned processing steps.

In order to find suitable dose for medical use of the TCEE (first embodiment) and the GLEE (second embodiment), the inventors of the present invention complete a first cell experiment. In the first cell experiment, the TCEE and the GLEE are taken to treat Human Umbilical Vein Endothelial Cells (HUVEC) for 48 hours. Please refer to FIG. 1, which shows a plot curve graph of extract concentration versus cell viability. From FIG. 1, it can easily find that, high-concentration TCEE (285.2 µg/mL) and GLEE (377.4 µg/mL) show inhibition effect to HUVEC.

Figure 2:
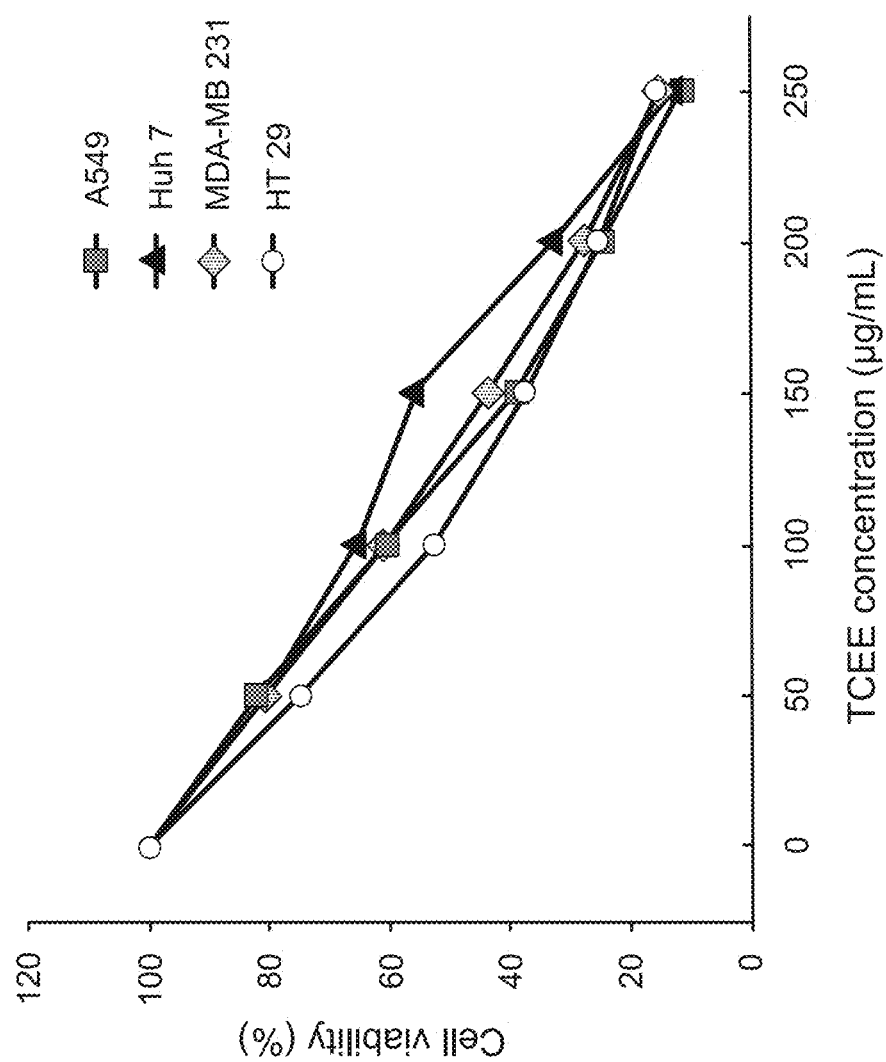
FIG. 2 shows a plot curve graph of TCEE concentration versus cell viability.

Continuously, the inventors of the present invention finish a second cell experiment. In the second cell experiment, the TCEE with different doses (0-250 µg/mL) are used to treat lung cancer cell A549, liver cancer cell Huh 7, breast cancer cell MDA-MB 231, and colorectal cancer cell HT 29. Please refer to FIG. 2, which shows a plot curve graph of TCEE concentration versus cell viability. From FIG. 2, it is able to find that, the TCEE can indeed lower the cell viability of lung cancer cell A549, liver cancer cell Huh 7, breast cancer cell MDA-MB 231, and colorectal cancer cell HT 29 down to 50%. In addition, the half maximal inhibitory concentration (IC50) of the TCEE for treating different cancer cells is integrated in following Table (1). Thus, the experimental data of second cell experiment have proved that the first embodiment (TCEE) of the pharmaceutical composition proposed by the present invention indeed shows a therapeutic effect to at least one kind of cancer cell.

TABLE (1)

| Cancer cell | IC50 of TCEE (µg/mL) |
| --- | --- |
| lung cancer cell A549 | 122.7 |
| liver cancer cell Huh 7 | 153.4 |
| breast cancer cell MDA-MB 231 | 130.6 |
| colorectal cancer cell HT 29 | 107.1 |

Figure 3:
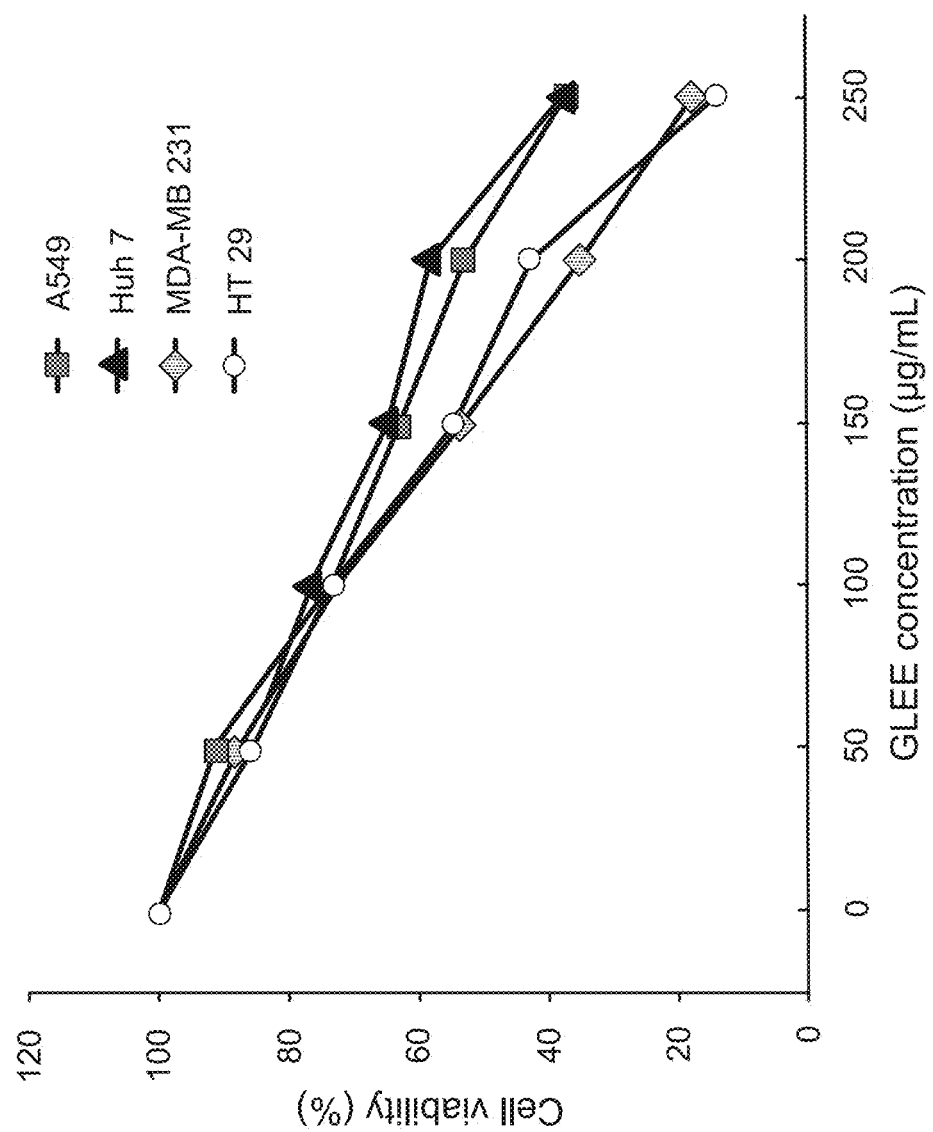
FIG. 3 shows a plot curve graph of GLEE concentration versus cell viability.

Furthermore, the inventors of the present invention also finish a third cell experiment. In the third cell experiment, the GLEE with different doses (0-250 µg/mL) are used to treat lung cancer cell A549, liver cancer cell Huh 7, breast cancer cell MDA-MB 231, and colorectal cancer cell HT 29. Please refer to FIG. 3, which shows a plot curve graph of GLEE concentration versus cell viability. From FIG. 3, it can find that, the GLEE can indeed lower the cell viability of lung cancer cell A549, liver cancer cell Huh 7, breast cancer cell MDA-MB 231, and colorectal cancer cell HT 29 down to 50%. In addition, the half maximal inhibitory concentration (IC50) of the GLEE for treating different cancer cells is integrated in following Table (2). Thus, the experimental data of second cell experiment have proved that the second embodiment (GLEE) of the pharmaceutical composition proposed by the present invention indeed shows a therapeutic effect to at least one kind of cancer cell.

TABLE (2)

| Cancer cell | IC50 of GLEE (µg/mL) |
|---|---|
| lung cancer cell A549 | 206.3 |
| liver cancer cell Huh 7 | 219.1 |
| breast cancer cell MDA-MB 231 | 157.9 |
| colorectal cancer cell HT 29 | 166.7 |

Besides the TCEE (first embodiment) and the GLEE (second embodiment), the present invention further proposes a third embodiment of the said pharmaceutical composition for adjunctively treating cancer. The third embodiment of the said pharmaceutical composition is a combination extract of the *Taiwanofungus camphorata* extract (i.e., the aforesaid TCEE) and the *Ganoderma lucidum* extract (i.e., the aforesaid GLEE). It is worth explaining that, the *Taiwanofungus camphorata* extract and the *Ganoderma lucidum* extract have a specific combining ratio, and the specific combining ratio is in a range from 1:11 to 10:1.

Figure 4:
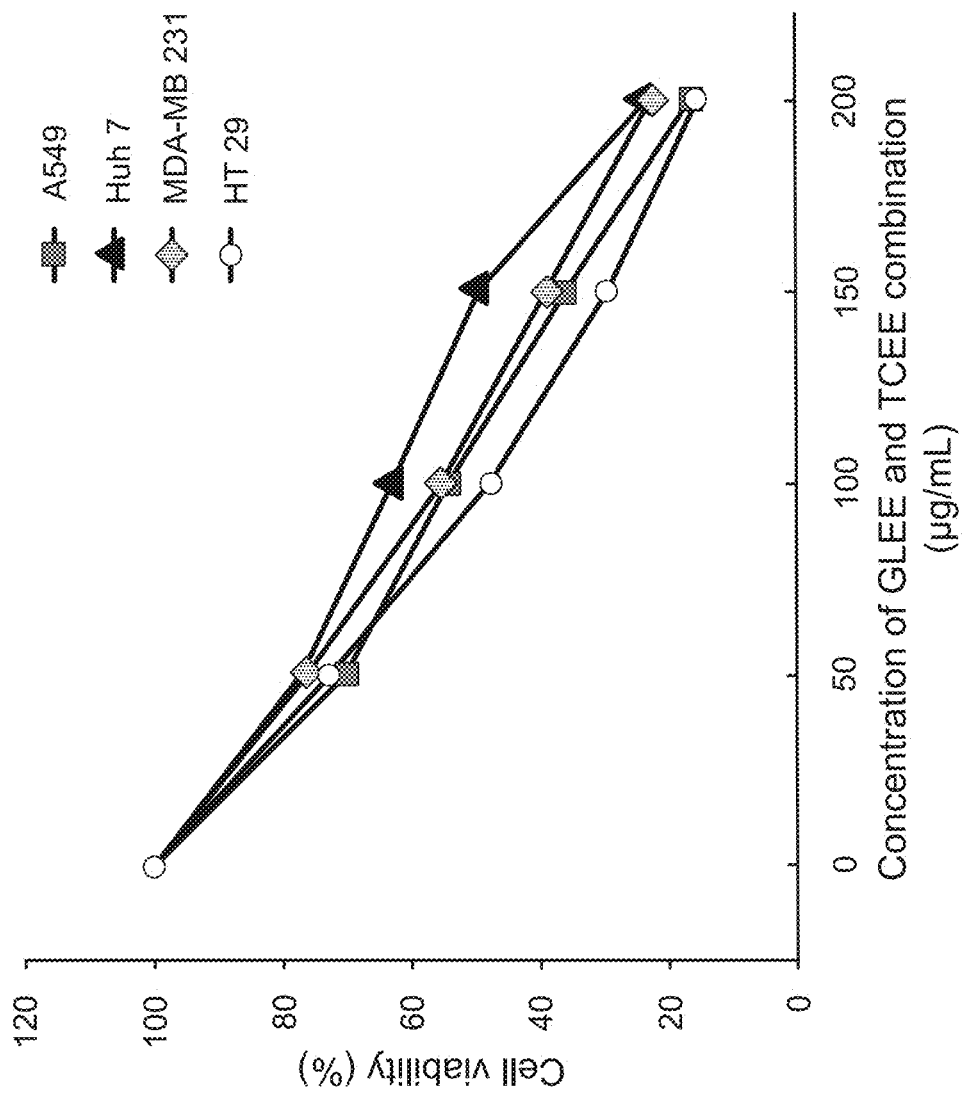
FIG. 4 shows a plot curve graph of concentration of GLEE and TCEE combination versus cell viability.

For determining whether the third embodiment of the pharmaceutical composition is able to shows therapeutic effect to cancer cells, the inventors of the present invention further finish a fourth cell experiment. Before starting the fourth cell experiment, the said combination extract is fabricated by mixing the TCEE and the GLEE by the a combining ratio of 3.65:1. Moreover, in the second cell experiment, the combination extract with different doses (0-250 µg/mL) are used to treat lung cancer cell A549, liver cancer cell Huh 7, breast cancer cell MDA-MB 231, and colorectal cancer cell HT 29. Please refer to FIG. 4, which shows a plot curve graph of concentration of GLEE and TCEE combination versus cell viability. From FIG. 4, it is able to find that, the combination extract can indeed lower the cell viability of lung cancer cell A549, liver cancer cell Huh 7, breast cancer cell MDA-MB 231, and colorectal cancer cell HT 29 down to at least 50%. In addition, the half maximal inhibitory concentration (IC50) of the combination extract for treating different cancer cells is integrated in following Table (3). Thus, the experimental data of second cell experiment have proved that the third embodiment (TCEE and GLEE combination) of the pharmaceutical composition proposed by the present invention indeed shows a therapeutic effect to at least one kind of cancer cell.

TABLE (3)

| Cancer cell | IC50 of combination extract (µg/mL) |
|---|---|
| lung cancer cell A549 | 111.1 |
| liver cancer cell Huh 7 | 146.4 |
| breast cancer cell MDA-MB 231 | 115.6 |
| colorectal cancer cell HT 29 | 96.2 |

It is worth noting that, the bio-engineers skilled in fabricating medically-used compositions or drugs can find an experimental result from Tables (1)-(3). The experimental result is that the combination extract (third embodiment) performs better cancer cell viability inhibiting effect than the TCEE (first embodiment) under the same treating does; moreover, the TCEE (first embodiment) shows better cancer cell viability inhibiting effect than the GLEE (second embodiment) under the same treating does. In summary, the combination extract is able to lower the cell viability of lung cancer cell A549, liver cancer cell Huh 7, breast cancer cell MDA-MB 231, and colorectal cancer cell HT 29 down to 50% by lower treating dose.

The above description is made on embodiments of the present invention. However, the embodiments are not intended to limit scope of the present invention, and all equivalent implementations or alterations within the spirit of the present invention still fall within the scope of the present invention.

What is claimed is:

1. A method of treatment of multiple different types kinds of cancer cells by using an identical pharmaceutical composition, consisting essentially of:

the pharmaceutical composition is provided by mixing an ethanol extract of *Taiwanofungus camphorata* (TCEE) and an ethanol extract of *Ganoderma lucidum* (GLEE) based on a mixing ratio of 3.65:1; and treating the multiple kinds of cancer cells including colorectal cancer cell HT 29, lung cancer cell A549, liver cancer cell Huh 7, and breast cancer cell MDA-MB 231 with the pharmaceutical composition by a specific dosage of 150 µg/mL, thereby exhibiting a therapeutic effect in reducing a cell viability of all of the cancer cells down to below or equal to 50%.

2. The method of claim 1, wherein the cancer cells constituted a cancer tumor that is selected from the group consisting of: lung cancer tumor, liver cancer tumor, breast cancer tumor, and colorectal cancer tumor.

\* \* \* \* \*